(12) United States Patent
Medri

(10) Patent No.: US 8,440,219 B2
(45) Date of Patent: May 14, 2013

(54) REDUCED-ODOR THIOL COMPOSITIONS

(75) Inventor: Mario W. Medri, Miami Lakes, FL (US)

(73) Assignee: Consumer Products Corp., Newark, NJ (US)

( * ) Notice: Subject to any disclaimer, the term of this patent is extended or adjusted under 35 U.S.C. 154(b) by 106 days.

(21) Appl. No.: 12/959,807

(22) Filed: Dec. 3, 2010

(65) Prior Publication Data

US 2011/0131928 A1   Jun. 9, 2011

Related U.S. Application Data

(62) Division of application No. 11/486,108, filed on Jul. 14, 2006, now abandoned.

(51) Int. Cl.
*A61K 47/44* (2006.01)
(52) U.S. Cl.
USPC .......................................... 424/439; 424/440
(58) Field of Classification Search .................. None
See application file for complete search history.

(56) References Cited

U.S. PATENT DOCUMENTS

| | | | | |
|---|---|---|---|---|
| 5,023,235 A | * | 6/1991 | N'Guyen et al. | 514/18.8 |
| 5,429,628 A | * | 7/1995 | Trinh et al. | 604/359 |
| 5,498,427 A | * | 3/1996 | Menasche | 424/678 |
| 6,045,823 A | * | 4/2000 | Vollhardt et al. | 424/450 |
| 6,153,204 A | * | 11/2000 | Fanger et al. | 424/401 |
| 6,689,728 B2 | * | 2/2004 | Diez | 510/147 |
| 6,790,451 B2 | * | 9/2004 | Nakanishi | 424/401 |

* cited by examiner

*Primary Examiner* — Nissa Westerberg
(74) *Attorney, Agent, or Firm* — Bingham McCutchen LLP

(57) ABSTRACT

The present invention provides compositions for and methods of delivering a therapeutically-effective dose of a malodorous, sulfide or disulfide group-containing compound, for example glutathione (reduced) and/or glutathione disulfide, in a vehicle that is effective to reduce the unpleasant odor and/or taste of the compound. The invention further provides methods for reducing the amount of oxidation occurring when sulfide group-containing compounds, such as glutathione, are incorporated into sugar and or sugar-free hard candies without subjecting the glutathione to thermal and or moisture degradation where degradation is expressed as oxidation. The invention further provides vehicle compositions including the protected sulfide group-containing compounds and their use as medicaments. The sulfide group-containing compounds are protected from degradation by their dispersion into fats, oils, and/or fractionated or partially hydrogenated oils prior to their blending into the vehicle.

16 Claims, No Drawings

REDUCED-ODOR THIOL COMPOSITIONS

CROSS-REFERENCE TO RELATED APPLICATIONS

This application is a divisional application of U.S. application Ser. No. 11/486,108, filed Jul. 14, 2006, the contents of which are incorporated herein by reference.

FIELD OF THE INVENTION

This invention relates to compositions for and methods of delivering a therapeutically-effective dose of a malodorous, sulfide (thiol) or disulfide group-containing compound, for example glutathione (reduced) and/or glutathione disulfide, in a vehicle that is effective to reduce the unpleasant odor and/or taste of the compound. The invention further relates to methods for reducing the amount of oxidation occurring when sulfide group-containing compounds, or thiols, such as glutathione, are incorporated into sugar and or sugar-free hard or soft candy vehicles.

BACKGROUND OF THE INVENTION

Glutathione (L-α-glutamyl-L-cysteinyl-glycine; GSH) is a well-known tri-peptide thiol found in virtually all cells. Glutathione disulfide (GSSG) is the oxidized dimmer of glutathione. Glutathione functions to reduce the disulfide linkages of proteins and other molecules, as an antioxidant, and is an essential compound in the gamma-glutamyl cycle, which is thought to effect transport of amino acids through cell membranes. Glutathione is also known to act as a cofactor in a variety of enzymatic reactions, including the glyoxylase reaction, the cis-trans isomerization of maleylacetoacetate to fumarylacetoacetate, and the formaldehyde dehydrogenase reaction.

Glutathione is synthesized by the method of Ozawa, Y. et al., Bull Chem, Soc. Jpn. 53: 2592 (1980). Alternatively, glutathione is isolate from yeast by the method fo Bloch, K. et al., Methods in Enzymology 3, 603 (1957). Glutahione disulfide (GSSG) is synthesized by the method of Bitny-Szlachto et al., Acta Biochim. Pol. 17, 175 (1970). Glutathione and its disulfide are also readily available commercially and inexpensive.

U.S. Pat. Nos. 6,013,632 and 6,107,281 to Jones et al., the disclosures of which are incorporated herein by reference in their entireties, disclose the effective use of glutathione, its derivatives, and pharmaceutically-acceptable salts of the same and of similar compositions specifically containing thiol, sulfide, disulfide and/or mercapten groups, including N-acetyl-L-cysteine, for the prophylaxis and treatment of influenza virus infections. Delivery is disclosed as being preferably carried out in the form of a lozenge, drinking solution, mouth rinse, or nasal spray for the purpose of coating the oral/nasal passages and mucous membranes of the subject Thiol-containing compounds, however, are notorious for their unpleasant odor and taste and so the use of thiol compounds such as glutathione in oral and nasal formulations has not been well received.

Glutathione and other thiol-containing compounds are most effective in the treatment and prophylaxis of influenza virus when administered in their reduced form, i.e., where thiol or sulfide (—SH) groups are present Furthermore, the sulfurous taste and smell of thiol compounds like glutathione increases with the amount of oxidation. However, such compounds are highly prone to oxidative degradation.

Degradation of reduced glutathione via oxidation is caused by many factors, the most significant of which are exposure to high temperature and water. It is well known by those skilled in the analytical arts that standard analytical solutions of pure glutathione in water solution must be prepared fresh every 4 hours due to the loss of concentration of reduced glutathione through oxidation. High temperature exposure causes oxidative degradation of glutathione even faster than exposure to water, and the higher the temperature the faster the thiol compound oxidizes. Long-time exposure to water at a relatively low temperature will generate similar levels of oxidation as exposure to high temperature for a short time.

This fact prevents the easy incorporation of thiol compounds into oral or nasal vehicles in highly reduced form. Glutathione cannot be added to a candy product vehicle during production in a water solution do to its instability in water. Further, such vehicles generally have an aqueous component themselves and are prepared using heat, thus accelerating the oxidation of the thiol-containing compounds incorporated therein. The thiol compounds tend to become oxidized during the product preparation phase and are thus not available in the final product to the patient in their more effective, highly reduced form. For example, glutathione tends to be converted to glutathione disulfide when being incorporated into a candy-base, i.e. a lozenge or cough drop, as the glutathione must be added while the aqueous candy base is in a hot, molten form.

Accordingly, there is therefore a need in the art for methods of preparing compositions containing thiol-containing compounds having a reduced sulfur odor and/or sulfur flavor, as well as compositions prepared by such methods, and there is a further need for methods of preparing compositions including thiol-containing compounds wherein the thiol-containing compounds are protected from degradation.

SUMMARY OF THE INVENTION

The present invention provides methods for diminishing an unpleasant smell or taste of a thiol compound and compositions containing thiol compounds having diminished unpleasant odors and tastes. The method involves blending a thiol compound into a fluidized fat or oil to produce a blend having a diminished unpleasant smell or taste of the thiol compound. Preferably, the thiol compound is glutathione, glutathione disulfide, ascorbate-2-phosphate, N-acetyl-L-cysteine. Whenever below that thiol compounds are discussed, it should be understood that the discussion includes derivatives of the thiol compounds or pharmaceutically acceptable salts of any of the foregoing, in any combination. The fluidized fat or oil is preferably a vegetable oil, mineral oil, animal fat, or any combination thereof, and the fat or oil may be partially or fully hydrogenated. More preferably, the vegetable oil is canola oil, cottonseed oil, soybean oil, sunflower oil, palm oil, coconut oil, Paramount™ C partially-hydrogenated palm kernel oil, or any combination thereof. The fluidized fat or oil preferably is essentially anhydrous.

The blending process of the present invention preferably occurs in fluidized fat or oil at a temperature of about 40° C. to about 90° C., and in the blend the thiol compound preferably comprises about 20 to about 70 percent by weight of the blend and the fats or oils preferably comprise about 80 to about 30 percent by weight of the blend. The thiol compound used in the blend is preferably provided as a powder having a particle size range of about 5 to about 500 microns.

In one preferred embodiment of the invention, the thiol compound is glutathione; the oil or fat is Paramount™ C partially-hydrogenated palm kernel oil, the ratio of glutathione to Paramount™ C partially-hydrogenated palm kernel oil is from about 55:45 to about 45:55, the glutathione is provided as a powder having a particle size range of about 80 to about 120 microns, and the blending occurs at about 70° C.

The present invention further provides a method for preventing oxidation of thiol groups in thiol compounds, comprising blending a thiol compound for which oxidation is to be prevented into a fluidized fat or oil; and preventing the oxidation of the thiol compound. Preferably, the thiol compound is glutathione, ascorbate-2-phosphate, N-acetyl-L-cysteine, or 20 derivatives or pharmaceutically acceptable salts of any of the foregoing, in any combination as described above.

The fluidized fat or oil is preferably a vegetable oil, mineral oil, animal fat, or any combination thereof, and the fat or oil may be partially or fully hydrogenated. More preferably, the vegetable oil is canola oil, cottonseed oil, soybean oil, sunflower oil, palm oil, coconut oil, Paramount™ partially-hydrogenated palm kernel oil, or any combination thereof, the blending occurs in fluidized fat or oil at a temperature of about 40° C. to about 90° C., and the fluidized fat or oil is essentially anhydrous.

In another embodiment of the invention, the thiol compound comprises about 20 to about 70 percent by weight of the blend and the fats or oils comprise about 80 to about 30 percent by weight of the blend. Preferably, the thiol compound is provided as a powder having a particle size range of about 5 to about 500 microns. In some embodiments, the thiol compound is glutathione, the oil or fat is Paramount™ C partially-hydrogenated palm kernel oil, the ratio of glutathione to Paramount™ C partially-hydrogenated palm kernel oil is from about 55:45 to about 45:55, the glutathione is provided as a powder having a particle size range of about 80 to about 120 microns, and the blending occurs at about 70° C.

In another embodiment of the invention, the blend is stored for later use by dividing the blend into aliquots; and storing the aliquots in essentially airtight containers.

Blends prepared as described may be used for preparing thiol compound-containing compositions having reduced sulfur odor and flavor. In one embodiment, a composition according to the present invention is prepared by blending a thiol compound into a fluidized fat or oil to produce a blend; adding the blend to a composition in preparation; and completing the preparation of the composition to produce a prepared thiol compound-containing composition having reduced sulfur odor and flavor.

Preferably, a composition according to the present invention comprises a carbohydrate. In some embodiments, the carbohydrate is sucrose, glucose, xylose, ribose, maltose, galactose, dextrose, fructose, corn syrup, hydrogenated glucose syrup, high fructose corn syrup, polydextrose, isomalt, maltitol, sorbitol, lactitol, mannitol, xylitol, hydrogenated starch hydrolysates, inulin, or any combination thereof. In some embodiments, the composition further comprises one or more sucrose derivatives, one or more amino acid-based sweeteners, one or more dipeptide sweeteners, saccharin and salts thereof, one or more acesulfame salts, one or more cyclamates, one or more steviosides, one or more dihydrochalcone compounds, thaumatin, glycyrrhizin, aspartame, neotarne, alitame, and any combination thereof. Preferably, the prepared thiol compound-containing composition has a residual water content of about 5% or less by weight.

In some embodiments, the composition further comprises a flavoring. Preferably, the flavoring is spearmint oil, peppermint oil, cinnamon oil, oil of wintergreen, lemon oil orange oil, grape oil, lime oil, grapefruit oil, apple essence, strawberry essence, cherry essence, pineapple essence, banana essence, raspberry essence, or any combination thereof. In some embodiments, the composition further comprises one or more drugs, one or more therapeutic or diagnostic compounds, one or more nutritional supplements, one or more botanicals, one or more herbal extracts, one or more antioxidants, or any combination thereof.

In a preferred embodiment, the thiol compound is glutathione, the oil or fat is Paramount™ C, the ratio of glutathione to Paramount™ C partially-hydrogenated palm kernel oil is from about 55:45 to about 45:55, the glutathione is provided as a powder having a particle size range of about 80 to about 120 microns, the blending occurs at about 70° C., the carbohydrate is isomalt, and the residual water content is about 3.5% or less.

The present invention further provides compound-containing compositions having reduced sulfur odor and flavor, comprising blends including one or more thiol compounds dispersed into fat or oil as described herein. In a preferred embodiment, the composition is a medicament and may be a cough drop or lozenge. The composition may be a hard or soft candy. In a preferred embodiment, the composition is a hard candy, the thiol compound is glutathione, the oil or fat is Paramount™ C partially-hydrogenated palm kernel oil, the ratio of glutathione to Paramount™ C partially-hydrogenated palm kernel oil is from about 55:45 to about 45:55, the glutathione has a particle size rang of about 80 to about 120 microns; the carbohydrate is isomalt, and the residual water content is about 3.5% or less.

DETAILED DESCRIPTION OF THE INVENTION

As noted above, thiol compounds such as glutathione are effective for the treatment of influenza virus infections and as well as effective for the prophylaxis of influenza virus infections. The glutathione is most effective when provided in its reduced form where sulfide, or thiol, (—SH) groups are present. Furthermore, the smell and taste perception of thiol compounds such as glutathione is of a disagreeable and unpleasant sulfurous smell and/or taste. Glutathione in its oxidized form (glutathione disulfide) smells and tastes even worse than glutathione in its reduced form. Accordingly, it is preferable to maintain the thiol compound in a highly reduced state.

Also as noted above, glutathione is prone to oxidation wherein the (—SH) groups of individual pairs of glutathione molecules react and oxidize by forming a disulfide group (—SS—). This oxidation of the compound reduces the effectiveness of the compound in the prevention and treatment of influenza virus infections and makes the smell and taste of a medicament containing such compounds less desirable. Thus, it is preferable that the thiol compound be preserved in a zero-oxidation form. Since heat and water are the primary culprits in causing oxidation of thiol compounds such as glutathione, to achieve the zero-oxidation objective it was discovered that adding glutathione to a fat or fatty-type mediating vehicle essentially devoid of water protects the thiol compound from thermal shock and degradation, including degradation due to exposure to water, when added to the final product.

The inventor has discovered that thiol compounds may be protected from degradation in the cooking process, as well as having their unpleasant tastes and odors diminished, by pre-blending the thiol compound with a fluidized fat or oil prior to addition to as final composition being prepared, e.g. a lozenge or cough drop. The temperature of fluidization will vary according to the type of fat or oil to be used, but preferably the blending occurs at a fluidizing temperature of about 40° C. to about 90° C., about 50° C. to about 80° C., about 60° C. to about 75° C. In particular, glutathione may be incorporated into a candy-based lozenge in highly-reduced form without significant malodors when the glutathione is blended into a partially hydrogenated vegetable oil, for example partially hydrogenated palm oil, which has been fluidized at about 70° C., prior to incorporation of this blend into the candy vehicle which will comprise the lozenge.

The ratio of thiol compound (e.g. glutathione) to oil or fat in the blend may vary depending on the type of oil or fat used and the desired effect. Thiol compound content in the blend can range from about 20 to about 70 percent, from about 30 to about 60 percent, or from about 45 to about 55 percent by weight of the blend while the fats or oils can vary from about 80 to about 30 percent, from about 70 to about 40 percent, or from about 55 to about 45 percent by weight of the blend. Typically, the oils and/or fats make up the bulk of the remainder of the blend apart from the thiol compound, though secondary ingredients may make up some proportion of the blend. Oils and fats used in the blends may be partially hydrogenated or fully hydrogenated and may contain mixtures of different oils or fats. Preferred oils are partially hydrogenated and fully hydrogenated vegetable oils, including canola oil, cottonseed oil, soybean oil, sunflower oil, palm oil, coconut oil, and combinations thereof, but may include other oils and/or fats including animal fats and mineral oil.

By this means, reduced thiol compounds, for example glutathione, may be added to a vehicle composed of molten hard candy, or of any type of carbohydrate-based vehicle, that after processing through a cooking/vacuuming system exhibits a residual moisture content of about 5% or less, 3.5% or less, or ranging from about 0.5 to about 5%, preferably about 0.5 to about 3%, and more preferably about 1 to about 2%, and even more preferably about 1.5%. One skilled in the confectionery arts will recognize that residual moisture content varies depending upon the type of candy composition being prepared; whereas hard candies generally require a moisture content of less than 5%, soft candies may have a residual moisture content of about 9% or less. While reduced thiol compounds may be presented in soft candy vehicles according to the present invention, the shelf life of such compositions will tend to be shorter than that for hard candies as the moisture content is higher and the moisture is more mobile within the structure of the composition, thus leading to increased degradation of the thiol compound under the influence of water.

The blends prepared above may also be cooled and stored prior to usage. The thiol compounds will exhibit significantly reduced or eliminated oxidation when stored in this manner. The stored blend may be used later with or without heating/ melting, depending upon the use anticipated. In a preferred embodiment of the invention, the cooled blend is divided into aliquots and stored in individual air-tight containers. Of course, one skilled in the art will recognize that division of the blend may be accomplished while the blend is still hot and allowed to cool in the individual storage containers.

Many candy-base ingredients are known in the art and may be used in the vehicle of the present invention. The vehicle preferably comprises one or more sugars, sugar syrups, sugar alcohols and/or sugar alcohol solids. Examples include, but are not limited to, sugars such as sucrose, glucose, xylose, ribose, maltose, galactose, dextrose, and fructose; syrups such as corn syrups, hydrogenated glucose syrups, high fructose corn syrups; polydextrose; and sugar alcohols such as isomalt, maltitol, sorbitol, lactitol and mannitol. The latter are also often in the form of syrups. Other ingredients that can yield a suitable hard candy type vehicle for the delivery of glutathione are hydrogenated starch hydrolysates, also know as HSH, and inulin, an oligosaccharide. One skilled in the art will appreciate that if a sugar or sugar alcohol solid is used in the vehicle, it should be first dissolved, for example, by heating in water or in another syrup, prior to being added to the mixture. Further, one skilled in the art will appreciate that the total amount of sugar in the vehicle will vary depending upon the combination of sugar sources used. For example, when sugar syrups are used, lower viscosity sugar syrups will produce a vehicle with less body and lower rigidity.

Preferably, the sugar/carbohydrate component of the candy vehicle is 100% isomalt, which is a type of hydrogenated maltitol. Such isomalt, being a sugar-free ingredient (meaning that it does not hydrolyze in the oral cavity) is preferred over other hard candy vehicles of the type composed of sugar and corn syrup. Combinations of sugars or sugar syrups are also suitable for use in the preparation of the vehicle. Examples of suitable combinations of syrups include, but are not limited to, isomalt syrup and high fructose corn syrup, a high DE corn syrup and high fructose corn syrup and maititol syrup and high fructose corn syrup.

The present invention also contemplates that, when the carbohydrate component of the vehicle is a modified starch, that a modified vegetable gum or cellulose may be included in the vehicle in order to improve the texture, lubricity and/or elasticity of the vehicle. These compounds can be used, for example, to increase the viscosity of the composition if it is warmed, thus reducing potential melting and lessening water activity which will help to improve the stability of the system in the event it is left in an excessively hot environment. Examples of modified vegetable gums or celluloses are provided above. The modified vegetable gum or cellulose can be included in the vehicle in amounts between about 0.01% and 0.8% by weight. In one embodiment, modified vegetable gum or cellulose is included in the vehicle in an amount between about 0.1% and about 0.7%.

The vehicle can optionally contain other additives such as sweeteners, flavorings, colorings, modified vegetable gums or celluloses, or a combination thereof. It will be readily apparent that additives for inclusion in the vehicle should be selected such that they do not affect the properties of the vehicle, do not exhibit substantial reactivity with the functional ingredients in the vehicle, and are stable during preparation of the vehicle.

The sweetener can be selected from a wide variety of suitable materials known in the art. Representative, but non-limiting, examples of sweeteners include: xylose, ribose, sucrose, mannose, galactose, fructose, dextrose, maltose, partially hydrolysed starch, lactose, maltodextrins, hydrogenated starch hydrolysate and mixtures thereof. In addition to these sweeteners, polyhydric alcohols such as sorbitol, mannitol, xylitol, and the like may also be incorporated. Alternatively, one or more artificial sweeteners can be used, for example, sucrose derivatives (such as Sucralose), amino acid based sweeteners, dipeptide sweeteners, saccharin and salts thereof, acesulfame salts (such as acesulfame potassium), cyclamates, steviosides, dihydrochalcone compounds, thaumatin (tatin), glycyrrhizin, aspartame, neotame, alitame, and mixtures thereof.

When an additional sweetener is used, it can be used in amounts as low as 0.01% by weight. The actual amount of sweetener required will be dependent on the type of sweetener selected and on the desired sweetness of the final product. Amounts of various sweeteners to be added to food products are well known in the art.

Suitable flavorings that can be added to the composition are known in the art and include, both synthetic flavor oils and oils derived from various sources, such as plants, leaves, flowers, fruits, nuts, and the like. Representative flavor oils include spearmint oil, peppermint oil, cinnamon oil; and oil of wintergreen (methylsalicylate). Other useful oils include, for example, artificial, natural or synthetic fruit flavors such as citrus oils including lemon, orange, grape, lime and grapefruit, and fruit essences including apple, strawberry, cherry, pineapple, banana, raspberry and others that are familiar to a worker skilled in the art.

The amount of flavoring agent employed is normally a matter of preference subject to such factors as concentration/dilution of the flavor stock, flavor type, base type and strength desired. In general, amounts of about 0.01% to about 5.0% by weight of a final product are useful, though greater or lesser amounts may be used as maybe determined by one skilled in the art. In one embodiment of the present invention, a flavoring agent is included in the vehicle in amounts of about 0.02% to about 3%. In another embodiment, the flavoring agent is added in amounts of about 0.03% to about 1.5%.

Colorings suitable for use in foodstuffs are well known in the art and can be optionally included in the vehicle to add aesthetic appeal. A wide variety of suitable food colorings are available commercially, for example, from Warner Jenkins, St. Louis, Mo. Where a synthetic coloring agent is used in the vehicle, the amount ranges from about 0.01% to about 2% by weight. In one embodiment of the present invention, a synthetic coloring agent is added to the vehicle in an amount between about 0.03% to about 1% by weight. A worker skilled in the art will appreciate that when a coloring agent derived from a natural source is used in the vehicle, an increased amount of the coloring agent is generally required to achieve the same effect as a synthetic coloring agent.

Some of the preferred thiol compounds useful in the compositions of the present invention include one or more compounds selected from the group consisting of glutathione, glutathione disulfide, and N-acetyl-L-cysteine, or pharmaceutically acceptable salt of any of these compounds. Those skilled in the art will recognize that other thiol compounds are useful as well.

The pharmaceutically-acceptable salts of the compounds (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepromonate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-napthalensulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, didbutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Glutathione, or any other thiol compound, is preferably defined in particle size ranging from about 5 to about 500 micron, preferably about 20 to about 200 microns, and more preferably about 80 to about 120 microns. Such selection of preferred particle size of glutathione is found to be best for taste perception during the slow dissolution process of the vehicle in the oral cavity which is induced by the mechanical motion of sucking onto the tablet. Slow dissolution in the oral cavity is preferred because it will allow the glutathione to release from the vehicle over an extended period of time. Being of small particle size it will not be subjectively perceived to be sandy or unpleasant. It is preferable that the glutathione dissolve as fast as possible into the saliva fluids present in the oral cavity to assure its effectiveness against the influenza virus infection.

The formulations of the present invention preferably deliver about 10 to about 100 mg of glutathione (or other thiol compound), more preferably about 20 to about 60 mg, and even more preferably about 40 mg of glutathione per unit dose, typically a 1.4 g piece/lozenge. The ratio of glutathione to base-vehicle is controlled for taste development in the presence of vegetable fat or blends of fats and oils, and can easily be determined by one in the art. As one skilled in the art will understand, appropriate dosage ranges may vary depending upon the size, weight, age, sex, etc. of the subject.

Preferably these compositions and formulations are prepared with suitable nontoxic pharmaceutically acceptable ingredients. These ingredients are known to those skilled in the preparation of oral or nasal dosage forms and some of these can be found in REMINGTON'S PHARMACEUTICAL SCIENCES, 17th edition, 1985, a standard reference in the field.

Lozenges can be prepared according to U.S. Pat. No. 3,439,089 and by other methods well known in the art.

All the ingredients contributing to the formation of the vehicle require dissolution and eventual processing through a cooking system that will concentrate the mass of saccharide vehicle base and eventually vacuum it to a residual moisture content of less than about 5% and preferably to about 1.5% while still at relatively high temperature. The molten candy mass can exit the candy cooker at about a temperature ranging from 250 to about 290° Fahrenheit, It is then cooled and exposed in a continuous or in as batch process to a known quantity of glutathione/fat blend in addition to the desired flavoring, coloring, and other secondary ingredients used to further define the finished product.

Without being bound by theory, it is postulated that the fat surrounding the reduced glutathione particles absorbs the thermal impact of entry into the candy-cooking process. The addition of the molten glutathione/fat blend preferably takes place on a continuously monitored system, and its point of entry into the process is at a point where the candy mass is on a thermal downturn. Additional ingredients may be added at this time as well. As the glutathione/fat blend, together with additional coloring, flavoring, and active ingredients (as provided below), comes into intimate contact with the candy vehicle, preferably isomalt, it is very well dispersed by thorough mechanical agitation. The fully blended candy mass is then rapidly cooled down to a temperature range typical in the candy making and candy forming art for a high speed continuous system or batch process.

The compositions according to the present invention may comprise one or more additional functional ingredients. The functional ingredients to be incorporated into the composition can be drugs, therapeutic and/or diagnostic compounds, nutritional supplements that fulfill a specific physiologic function or promote the health an/or well-being of the consumer, botanicals or herbal extracts, and the like.

A variety of drugs or therapeutic and/or diagnostic compounds are suitable for use with the present composition. Representative examples include, but are not limited to, anti-tumour compounds such astamoxifen, doxyrubicin, taxol, cisplatin; anti-viral compounds such as ddI and ddA, anti-inflammatory compounds such as NSAIDs and steroids; antibiotic compounds such as antifungal and antibacterial compounds; cholesterol lowering drugs, anti-hypertensive drugs, vasoconstrictors, sedatives, antihistamines, decongestants, expectorants, and antinauseants and contrast agents for medical diagnostic imaging.

One or more of the functional ingredients included in the composition can be a nutritional supplement. Illustrative, but non-limiting, examples of nutritional supplements suitable for use with the composition according to the present invention include, probiotic bacteria, prebiotics, vitamins, enzymes, co-enzymes, cofactors, antioxidants, minerals and mineral salts, amino-acids and amino acid derivatives (for example, dimethylglycine), peptides, proteins, gums, carbohydrates, phytochemicals, dextroses, phospholipids, other trace nutrients, oxygenators, brain-stimulating substances, energy providers, metabolic intermediates, hormones, botanical extracts, fatty acids (for example, linoleic acid or conjugated linoleic acid), oat beta-glucan or other functional fibres, carnitine, bicarbonate, citrate, or combinations thereof.

Probiotic microorganisms in the form of live microbial nutritional supplements and which are recognized as conferring a beneficial effect on an animal can be incorporated into the composition. Probiotic microorganisms are microorganisms which beneficially affect a host by improving its intestinal microbial balance (see, for example, Fuller, R; 1989; J. Applied Bacteriology, 66: 365 378). Beneficial effects of probiotic microorganisms include activation of the immune system, prevention of the bacterial overgrowth by pathogens, prevention of diarrhoea and/or restoration of intestinal flora. Examples of probiotic microorganisms include, but are not limited to, *Bifidobacterium* (such as *Bifidobacterium longum* B129, *Bifidobacterium longum* B128, *Bifidobacterium adolescentis* Bad4, and *Bifidobacterium lactis* BbI2), *Lactobacillus* (such as, *Lactobacillus johnsonii* and *Lactobacillus paracasei*), *Streptococcus* and Saccharomyces. Typically, the microorganism is added to the vehicle in a spray dried or freeze-dried form.

Many probiotic bacterial strains have been deposited under the Budapest Treaty at the Collection Nationale de Cultures de Microorganismes (CNCM), Institut Pasteur, 28 rue du Docteur Roux, 75724 Paris Cedex 15, France. For example, *Lactobacillus johnsonii* (NCC 533) has been deposited on 30 Jun. 1992 under reference CNCM I-1225, *Lactobacillus paracasei* (NCC 2461) has been deposited on Dec. 1, 1999 under reference CNMC I-2116, *Bifidobacterium longum* (B129) (NCC490) has been deposited on 15 Mar. 1999 under reference CNCM I-2170, *Bifidobacterium longum* (B128) (NCC481) has been deposited on 15 Mar. 1999 under reference CNCM I-2169, and *Bifidobacterium adolescentis* (Bad4) (NCC251) has been deposited on 15 Mar. 1999 under CNCM I-2168. *Bifidobacterium lactis* (BbI2) maybe obtained at Hanzen A/S, 10 12 Boege Alle, P.O. Box 407, DK-2970.

The amount of probiotic incorporated into the composition will vary according to the specific needs. Typically, the amount of lactic acid bacteria in one unit of the composition is between $10^2$ and $10^{12}$ count/gram, for example, between $10^7$ and $10^{11}$ count/gram, or between $10^8$ and $10^{10}$ count/gram.

Prebiotics can be delivered alone or in combination with probiotic bacteria in he composition. Prebiotics comprise carbohydrates, generally oligosaccharides, and have the ability to resist hydrolysis by enzymes in the animal digestive tract and thus can reach the colon undegraded to provide a carbohydrate substance particularly suited to growth of probiotic bacteria. Oligosaccharides may be produced from glucose, galactose, xylose, maltose, sucrose, lactose, starch, xylan, hemicellulose, inulin, or a mixture thereof. Purified commercially available products such as fructo-oligosaccharide contain greater than about 95% solids in the form of oligosaccharides. Prebiotics often comprise a mixture of fructooligosaccharide and inulin, for example, PREBI01® (fructooligosaccharide/inulin blend commercialized by Nestle) or a mixture of commercially available RAFTILOSE® (fructooligosaccharaide) and RAFTILINE® (inulin), both of which are commercialized by Orafti. A prebiotic of this kind has been demonstrated to improve the response of the immune system.

Other suitable nutritional supplements include vitamins and minerals that the body is usually not capable of synthesizing and which are necessary for ensuring normal growth and/or daily body maintenance. In the context of the present invention, the vitamins can be hydrosoluble or liposoluble vitamins. Examples includes, but are not limited to, Vitamin A (axerophtol or retinol), Vitamin D, Vitamin E (alpha-tocopherol), Vitamin K, Vitamin B and/or PP (niacinamide or nicotinic acid amide) and Vitamin C (L-ascorbic acid). The dosage of vitamins in the composition can be adapted to specific needs. In general, one unit of the composition may contain a fraction of the recommended daily amount (RDA) of the desired vitamin. For example, assuming a daily consumption of five units of the composition, and following U.S. RDA recommendations, Vitamin A can be used up to 160 µg typically between 70 µg and 90 µg a single unit; Vitamin C up to 12 mg typically between 5 mg and 7 mg a single unit; Vitamin E up to 2 mg typically between 0.8 mg and 1.2 mg a single unit; Vitamin D up to 1 µg typically between 0.4 µg and 0.6 µg a single unit; Vitamin B1 up to 0.28 mg typically between 0.12 mg and 0.15 mg a single unit.

The present invention is also directed to compositions of the present invention with one or more antioxidants. For example, glutathione and glutathione disulfide, or any other composition of the present invention, may be effectively administered, whether at periods of pre-exposure or post-exposure or both, in combination with effective amounts of one or more of the antioxidants listed below: Vitamin A, Vitamin E, Vitamin K, Copper (as cupric oxide), Zinc (zinc oxide), Iron (Ferrous Salt), Selenium (Sodium Selenate), Beta-carotene, polyphenols, flavinoids, including flavanols, such as catechin or quercetin, and flavanones such as eriodictyol, Diterpenoids, such as carnosic acid, or carnosol, Phenolic acids, e.g., rosmarrinic acid, caffeic acid, coumaric acid, or cinnamic acids, Coenzyme Q10, Probucol, Carotenoids, such as astaxanthin or lycopene, Alpha-lipoate, and urate.

Antioxidants can be delivered using the composition of the present invention, alone or in combination with other functional agents, such as glutathione, peroxidase, superoxide dismutase, catalase, co-enzyme Q10, honey tocopherols and other tocopherols, lycopenes, beta-carotene or other carotenoids, quertin, rutin, flavonoids, catechins, anthocyanes, eleutherosides and ginsenosides. Some of these antioxidants may be found in significant amounts in plant extracts. Examples include Ginko Biloba leaves that contain Gingko flavanoids, Blueberry fruits that contains anthocyanids, Ginseng roots which contains ginsenosides, Eleutherococcus roots which contains eleutherosides. The biologically active agent may also be a phytochemical such as polyphenol, procyanidin, phenolic acid, catechin oz epicatechin, isoflavone, terpene or other phytonutritive plant material.

Suitable minerals include macro-nutrients such as sodium, potassium, calcium, magnesium, phosphorus or oligo-elements such as iron, zinc, copper, selenium, chromium, iodine or a combination thereof. Macro-nutrients are known to play an essential role in complex metabolisms of the body such as in cellular cation exchange, for example, calcium is an essential constituent of the skeleton. Following ED RDA recommendations and assuming, for instance, an average daily consumption of 5 units of the composition. Calcium may be used in amounts of up to 160 mg, typically between 60 mg and 90 mg in a single unit.

Trace elements are minerals present in the human body in quantity of usually less than 5 g. An example of a trace element is zinc, which has antioxidant properties, helps in the synthesis of metallothionein, is an essential factor for protein synthesis and helps improve the function of the immune system. Following ED RDA recommendations and assuming a daily consumption of 5 units of the composition, zinc may be used in amounts of up to 3 mg per unit, typically between 1.3 mg and 1.7 mg.

Selenium is also an antioxidant and is a co-factor for glutathione peroxidase. Selenium is known to contribute to the integrity of muscles and sperm and also plays a role in hepatic metabolism. Selenium deficiencies may lead to sever cardiac, bone or neuromuscular damage. For example, following the U.S. RDA recommendations and assuming a daily consumption of 5 units of the composition, Selenium maybe used in amounts of up to 11 μg per unit, typically between 4 μg and 6 μg in humans.

Other nutritional supplements include amino acids, di-peptides or polypeptides or proteins or essential fatty acids. A suitable example of an amino acid is glutamine which provides fuel to gastro-intestinal and immune cells, reduces bacterial translocation and helps prevent muscle loss and improves nitrogen balance. Examples of peptides are the glycopeptides of lactic origin active in inhibiting the adhesion of the bacteria responsible for dental plaque and caries; More particularly, dental and anti-plaque caries agents of this type comprise active principle(s) selected from kappa-caseinoglycopeptides and deacylated derivatives thereof (also known as "CGMP"). Such active principles have an effectiveness on the dental plaque only after a few seconds in the mouth (see, for example, European Patent Number EP283675). Other peptides include phosphopeptides or salts thereof having anticarie properties such as those having from 5 to 30 amino acids including the sequence A-B-C-D-E where, A, B, C, D and E being independently phosphoserine, phosphothreonine, phosphotyrosine, phosphohistidine, glutamate and aspartate and compositions particularly compositions to teeth including same (see, for example, U.S. Pat. No. 5,015,628).

Other examples of polypeptides are cysteine, acetylcysteine, cysteine methionine or a combination thereof. Cysteine and its derivatives are known to aid in defence against oxidative stress and in protein synthesis.

Other nutritional supplements include creatine, caffeine, bee pollen, Royal jelly, chitosan, chondroitin, functional fibres, phospholipids, enzymes known to aid digestion (such as papain, bromelain and lipases), shark cartilage extracts, glucosamine, methylsulponylmethane (MSM), pregnenolone, Brewer's yeast, blue green algae and the like.

The nutritional supplement can be a botanical extract, such as guarana, Gingko biloba, kola nut, goldenseal, Goto kola, schizandra, elderberry, St. John's Wort, valerian and ephedra and ephedra alkaloids, evening primrose oil, beta-sitosterol, cafestol, D-limonene, kabweol, nomilin, oltipraz, sulphoraphane, tangeretin, black tea, white tea, java tea, folic acid, garlic oil, fibre, jojoba, bitter melon, green tea extract, lemon oil, mace, licorice, menthol, onion oil, orange oil, rosemary extract, milk thistle extract, Echinacea, Siberian ginseng or Panax ginseng, lemon balm, Kava Kava, Yerba Mat, bilberry, soy, grapefruit, seaweed, hawthorn, lime blossom, sage, clove, basil, curcumin, taurine, wild oat herb, dandelion, gentian, aloe vera, hops, cinnamon, peppermint, grape chamomile, fennel, marshmallow, ginger, slippery elm, cardamon, coriander, anise, thyme, rehmannia, eucalyptus, menthol, citrus aurantium and schisandra.

Typically, the total amount of functional ingredients constitutes less than about 25% by weight of a composition. In one embodiment of the present invention, the total amount of 5 functional ingredients constitutes between about 5% and about 20% by weight of a composition. In another embodiment, the total amount of functional ingredients constitutes between about 5% and about 20% by weight of a composition.

Selection of appropriate functional ingredients for incorporation into the compositions for administration to a given animal is considered to be within the ordinary skills of a worker in the art and it is understood that functional agents suitable for administration to humans may differ from those suitable for other animals. Furthermore, it will be apparent that inappropriate combinations of functional agents, for example, those that interact with each other, should not be included in a composition.

Functional ingredients are incorporated into the composition at levels sufficient to affect the structure or function of the body when taken regularly. Such levels are known in the art or can readily be determined by a skilled technician. It is understood that the total daily intake may be based on administration of one unit of the composition, or it may be based on administration of more than one unit. The amount of functional ingredients in the final product will thus vary depending on the format of the units and the number to be administered daily.

EXAMPLE 1

| Composition of Glutathione Lozenge With Isomalt | |
|---|---|
| Isomalt | 91.789 |
| Glutathione powder | 2.860 |
| Artificial sweetener | 0.550 |
| FD&C coloring | 0.001 |
| Partially hydrogenated Palm oil | 3.000 |
| Flavoring ingredient | 0.300 |
| Residual moisture | 1.500 |

All amounts are provided as a weight percentage of the final product.

As described in formula of Example 1, isomalt can be substituted by oligosaccharides, maltitol syrups, or hydrogenated starch hydrolysates, among other compounds as described above, on a 1:1 replacement ratio for the delivery of glutathione.

EXAMPLE 2

| Composition of Glutathione Lozenge With Sorbitol | |
| --- | --- |
| Sorbitol | 91.989 |
| Glutathione powder r | 2.860 |
| Artificial sweetener | 0.350 |
| FD&C coloring | 0.001 |
| Partially hydrogenated Palm oil | 3.000 |
| Flavoring ingredient | 1.300 |
| Residual moisture | 1.500 |

All amounts are provided as a weight percentage of the final product.

EXAMPLE 3

| Composition of Glutathione Lozenge With Sugar/Corn Syrup-Based Vehicle | |
| --- | --- |
| Sugar granular | 45.419 |
| Corn syrup solids | 45.419 |
| Glutathione powder | 2.860 |
| FD&C coloring | 0.002 |
| Partially hydrogenated Palm oil | 3.000 |
| Flavoring ingredient | 0.300 |
| Residual moisture | 3.000 |

All amounts are provided as a weight percentage of the final product.

EXAMPLE 4

| Preparation of Glutathione/Fat Blend Formula A | |
| --- | --- |
| Paramount ™ C (partially hydrogenated palm oil) | 51.2 |
| Glutathione (reduced) (powder at 80-120 microns) | 48.8 |

The reduced glutathione is prepared in a fine powder having a particle size of about 80 to 120 microns; this powder is added to a molten, partially-hydrogenated palm kernel oil (known in the candy trade as Paramount™ C partially-hydrogenated palm kernel oil), or any of its hydrogenated fractions or equivalents characterized by having a melting point of about 80 to about 120° Fahrenheit and preferably about 90 to about 100° Fahrenheit.

In a steam-jacketed stainless steel vessel equipped with agitation add the Paramount™ C partially-hydrogenated palm kernel oil and heat it to 160 to 180° F. While agitating the molten fat, slowly add the glutathione powder. The temperature should be maintained at or slightly above 150° F. to avoid thickening of the admixture. This warm blend should be used within the production time required. In the fat-blended state, glutathione will not degrade or oxidize.

EXAMPLE 5

Preparation of Cough Drops Containing Glutathione

Candy base ingredients: Sorbitol kg 55.0, aspartame kg 1.0, Wild cherry imitation flavor gm 60.0. Medicament Mixture: Partially hydrogenated vegetable oil kg 2.75, Glutathione kg 5.0, Citric Acid kg 60.

In preparing the candy base, the sorbitol and aspartame are dissolved in 5.5 liters of water and mixed well. At this point, any desired dye may be added to impart the required color. The dye must be dissolved thoroughly.

The above mixture is placed in a steam-jacketed kettle which is heated to 125° C., from which it is pumped into a storage vessel that feeds a continuous cooker. As the syrup passes through a coil in the cooker, it reaches a temperature of 125-150° C. and is then fed into a receiving kettle maintained at 28-29 inches of vacuum by means of a steam vacuum ejector for a period of about 6-7 minutes. During this period water is removed until it is reduced to about 3% or less and a suitable molten candy base is formed. The candy base then is permitted to cool slowly.

The glutathione, citric acid and imitation flavor in powdered form are added to the fluidized partially hydrogenated vegetable oil at about 70° C. and mixed thoroughly. The warm fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 6

Preparation of Cough Drops Containing GSSG

Candy base ingredients: Sugar (medium fine granules) kg 35.0 Corn syrup 43° Baume kg 21.0 Medicament Mixture: Partially hydrogenated coconut oil kg 2.75, GSSG kg 5.0, Citric Acid kg 60, Wild cherry imitation flavor gm 60.0.

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steam-jacketed kettle which is heated to 125° C., from which it is pumped into a storage vessel that feeds a continuous cooker. As the syrup passes through a coil in the cooker, it reaches a temperature of 125-150° C. and is then fed into a receiving kettle maintained at 28-29 inches of vacuum by means of a steam vacuum ejector for a period of about 6-7 minutes. During this period water is removed until it is reduced to about 1.5% or less and a suitable molten candy base is formed. The candy base then is permitted to cool slowly.

The glutathione disulfide, citric acid and imitation flavor in powdered form are added to the fluidized partially hydrogenated coconut oil at about 70° C. and mixed thoroughly. The warm fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 7

Preparation of Cough Drops Containing GSH and Ascorbate-2-Phosphate

Candy base ingredients: Sugar (medium fine granules) kg 35.0, Corn syrup 43° Baume kg 21.0, Wild cherry imitation flavor gm 60.0. Medicament mixture: Paramount™ C partially-hydrogenated palm kernel oil kg 2.75, GSH kg 2.5, Ascorbate-2-phosphate kg 2.5, Citric acid kg 6.0.

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steam-jacketed kettle which is heated to 125° C., from which it is pumped into a storage vessel that feeds a continuous cooker. As the syrup passes through a coil in the cooker, it reaches a temperature of 125-150° C. and is then fed into a receiving kettle maintained at 28-29 inches of vacuum by means of a steam vacuum ejector for a period of about 6-7 minutes. During this period water is removed until it is reduced to about 2% or less and a suitable molten candy base is formed. The candy base then is permitted to cool slowly.

The medicament, citric acid and imitation flavor in powdered form are added to the fluidized Paramount™ C partially-hydrogenated palm kernel oil at about 70° C. and mixed thoroughly. The hot fluid mixture is rapidly added to the molten candy base (the temperature of which has been reduced to about 100° C., or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass, which then may be formed into any desired shape for dispensing a unit dosage of the medicament.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way.

The embodiments of the invention in which an exclusive property or privilege is claimed are defined as follows:

1. A method for diminishing an unpleasant smell or taste of a thiol compound, comprising:
    forming a blend by blending a thiol compound into a fluidized fat or oil at a temperature of about 40° C. to about 90° C. to produce a blend having a diminished unpleasant smell or taste of the thiol compound, wherein the thiol compound is provided as a powder having a particle size range of about 5 to about 500 microns, and the thiol compound comprises about 20 to about 70 percent by weight of the blend and the fats or oils comprise about 80 to about 30 percent by weight of the blend; and
    incorporating the blend into an ingestible product.

2. The method of claim 1, wherein the thiol compound is glutathione, glutathione disulfide, N-acetyl-L-cysteine, derivatives of any of the foregoing, or pharmaceutically acceptable salts of any of the foregoing, in any combination.

3. The method of claim 1, wherein the fluidized fat or oil is a vegetable oil, mineral oil, animal fat, or any combination thereof.

4. The method of claim 1, wherein the fat or oil is partially or fully hydrogenated.

5. The method of claim 3, wherein the vegetable oil is canola oil, cottonseed oil, soybean oil, sunflower oil, palm oil, coconut oil, partially hydrogenated palm kernel oil, or any combination thereof.

6. The method of claim 1, wherein the ingestible product includes a candy base.

7. The method of claim 1, wherein the thiol compound is glutathione, the fat or oil is partially hydrogenated palm kernel oil, the ratio of thiol to fat is between about 55:45 and 45:55, the particle size range is about 80 to 120 microns, and the temperature is about 70° C.

8. The method of claim 1, wherein the thiol compound is glutathione, the oil or fat is partially hydrogenated palm kernel oil, the ratio of glutathione to partially hydrogenated palm kernel oil is from about 55:45 to about 45:55, the glutathione is provided as a powder having a particle size range of about 80 to about 120 microns, and the blending occurs at about 70° C.

9. A method for preventing oxidation of thiol groups in thiol compounds, comprising:
    forming a blend by blending a powdered thiol compound for which oxidation is to be prevented into a fluidized fat or oil at a temperature of about 40° C. to about 90° C.; and
    incorporating the blend into an ingestible product.

10. The method of claim 9, wherein the thiol compound is glutathione, N-acetyl-L-cysteine, derivatives of any of the foregoing, or pharmaceutically acceptable salts of any of the foregoing, in any combination.

11. The method of claim 9, wherein the fluidized fat or oil is a vegetable oil, mineral oil, animal fat, or any combination thereof.

12. The method of claim 9, wherein the fat or oil is partially or fully hydrogenated.

13. The method of claim 11, wherein the vegetable oil is canola oil, cottonseed oil, soybean oil, sunflower oil, palm oil, coconut oil, partially hydrogenated palm kernel oil, or any combination thereof.

14. The method of claim 9, wherein the thiol compound comprises about 20 to about 70 percent by weight of the blend and the fats or oils comprise about 80 to about 30 percent by weight of the blend.

15. The method of claim 9, wherein the thiol compound is provided as a powder having a particle size range of about 5 to about 500 microns.

16. The method of claim 9, wherein the thiol compound is glutathione, the oil or fat is partially hydrogenated palm kernel oil, the ratio of glutathione to partially hydrogenated palm kernel oil is from about 55:45 to about 45:55, the glutathione is provided as a powder having a particle size range of about 80 to about 120 microns, and the blending occurs at about 70° C.

* * * * *